United States Patent [19]

Carlson

[11] Patent Number: 5,358,967
[45] Date of Patent: Oct. 25, 1994

[54] WOOL PROTECTING COMPOSITONS AND METHODS

[75] Inventor: Glenn R. Carlson, North Wales, Pa.

[73] Assignee: Rohm and Haas Company, Philadelphia, Pa.

[21] Appl. No.: 87,581

[22] Filed: Jul. 6, 1993

[51] Int. Cl.$^5$ .............................................. A01N 37/18
[52] U.S. Cl. .................................................... 514/615
[58] Field of Search ........................................ 514/615

[56] References Cited

U.S. PATENT DOCUMENTS

| | | | |
|---|---|---|---|
| 4,399,280 | 8/1983 | de Sousa et al. | 544/301 |
| 4,985,461 | 1/1991 | Hsu et al. | 514/615 |
| 5,110,986 | 5/1992 | Kelly | 564/149 |
| 5,117,057 | 5/1992 | Hsu et al. | 564/149 |

OTHER PUBLICATIONS

CA117 (1): 2804y: JP04005203, Uehata et al., 1992.
CA114 (19): 180361x: GB 2231268, Carlson et al., 1990.

Primary Examiner—Richard L. Raymond
Assistant Examiner—Mary C. Cebulak
Attorney, Agent, or Firm—Joseph F. Leightner

[57] ABSTRACT

The present invention is a composition comprising an effective amount of an N'-alkyl-N'-(3,5-dimethylbenzoyl)-N-(substituted benzoyl)-hydrazine to treat wool for protection from keratin digesting insects, and an insect-proofing method using such compounds. The compositions and methods have particular application in treating wool.

6 Claims, No Drawings

WOOL PROTECTING COMPOSITONS AND METHODS

BACKGROUND OF THE INVENTION

The present invention relates to an insect-proofing composition and an insect-proofing method. More specifically, the present invention relates to an insect-proofing composition comprising N'-alkyl-N'-(3,5-dimethylbenzoyl)-N-(substituted benzoyl)hydrazine as an active ingredient and an insect-proofing method using such compounds. The compositions and methods have particular application in treating wool.

Several hundred million kilos of wool are treated with mothproofing agents every year. Much of this goes into carpets, apparel, bed wear and upholstery. The key pests are various species of clothing moths. The mothproofing, wool-treating agent(s) can be applied during fibre manufacture, usually during the dyeing process.

Several characteristics are desired in a wool-treating agent. For example, the agent must be efficacious against the pests which can damage wool. Typical wool pests which feed on the keratin in wool are *Lepidoptera larvae*, e.g. Tineola species and Tinea species, and *Coleoptera larvae*, e.g. Anthrenus species and Attagenus species. The agents used should be stable to hydrolysis, washfast, and lightfast for protecting wool in the processed state. The treated wool has use in woolen textiles such as blankets, wool carpets, woolen underwear, woolen clothing, knits and blends with material or artificial fibres.

Other beneficial properties of wool-treating agents include low volatility and dry-cleaning fastness. Yet another important property is chemical loading onto the wool, which can be environmentally beneficial by reducing the amount of treatment agent which passes through to waste streams. One measure of loading characteristics is the log P value of the compound, which log P denotes the relative lipophilic value as calculated by C. Hanach et al., in J. Med. Chem. 16, 1207 (1973). Chemical stability during chemical loading is important since the loading may be performed under dyeing conditions (e.g. a pH range to 2 to 7, temperatures of 100° C., dyeing time of one to five hours). Efficacy must be retained after subjection of these harsh conditions as well as in the presence of down-process lubricants, surfactants and other additives. A major wool-treating agent heretofore has been pyrethroids, such as permethrin. Permethrin use, however, has become problematic in its contamination of the aquatic environments which are the recipients of the wool-treatment waste streams.

U.S. Pat. Nos. 4,985,461 and 5,117,057 disclose insecticidal N'-substituted-N,N'-diacylhydrazines which are disclosed as having utility against Lepidoptera pests. New wool-treatment agents which possess the required efficacy to protect wool from pests while having favorable process, environmental and toxicological properties are desired and sought.

SUMMARY OF THE INVENTION

The present invention is a composition comprising an effective amount of an N'-alkyl-N'-(3,5-dimethylbenzoyl)-N-(substituted benzoyl)-hydrazine to treat wool for protection from keratin digesting insects, and an insect-proofing method using such compounds. The compositions and methods have particular application in treating wool.

EMBODIMENT OF THE INVENTION

Compositions of the present inventions are compositions comprising an effective amount of an N'-alkyl-N'-(3,5-dimethylbenzoyl)-N-(substituted benzoyl)-hydrazine to treat wool for protection from keratin digesting insects. More particularly, the present invention are compositions comprising an effective amount of N-(2-A-3-B-4-C-benzoyl)-N'-D-N'-(3,5-dimethylbenzoyl)-hydrazine, wherein A, B, and C are independently selected from halogens, $(C_1-C_4)$alkyls and $(C_1-C_4)$alkoxys, provided that one or two of A, B or C is hydrogen, and wherein D is a branched $(C_4-C_5)$alkyl. Preferred halo's are bromo, chloro and fluoro, more preferably chloro and fluoro, and even more preferably chloro. The $(C_1-C_4)$alkyls which can be represented by A, B or C are straight or branched alkyls optionally substituted with one or more halo's; preferably straight, unsubstituted alkyls; more preferably methyl or ethyl. The $(C_1-C_4)$ alkoxys are preferably straight alkoxys; more preferably methoxy or ethoxy; even more preferably methoxy. The preferred substituent pattern on the substituted benzoyl is preferably at most only one halogen, alkyl or alkoxy.

The D moiety which is the N'-alkyl group is a branched $(C_4-C_5)$alkyl; more preferably neo-pentyl or tert-butyl; even more preferably tert-butyl.

The preferred compounds are N'-(3,5-dimethylbenzoyl)-N-(4-ethylbenzoyl)-N'-(tert-butyl)-hydrazine and N-(2,3-dimethylbenzoyl)-N'-(3,5-dimethylbenzoyl)-N'-(tert-butyl)-hydrazine.

The composition of the present invention comprises one or more hydrazine(s) of the present invention which has a suitable log P value to permit an effecting loading of the hydrazine compound onto the treated fibre. Preferably the log P value ranges from about 2 to about 6, more preferably from about 4 to about 6.

The compositions of the invention can be used for protecting keratinous material against insects that feed on keratin, e.g. against *Lepidoptera larvae* such as Tineola spec. and Tiena spec., and also Coleoptera larvae, e.g. Anthrenus spec. and Attagenus spec. The compositions are most suitable for proofing keratinous material against feeding damage by insects, especially for providing such material with a washfast and lightfast protective finish against insects such as moths. The keratinous material to be proofed can be both in the raw and in the processed state, for example raw or processed sheep's wool or products made of other animal hairs, hides, furs and feathers. Preferably, an optimal amount is used in which the desired efficacy is attained while loosing a minimal amount of the hydrazine because of a failure of the excess to load onto the wool. Those skilled in the art can readily determine the amount to be used under the parameters of the particular wool fibre and manufacturing (e.g. dyeing) process conditions usable for such fibre. The processes usable are known in the art wherein an insecticidally active compound is loaded onto a fibre. For example, see U.S. Pat. No. 4,399,280 or the processes described hereinafter.

A particularly important feature is the effectiveness of the compositions of the invention against the larvae of the webbing clothes moth (*Tineola bisselliella*), the common clothes moth (*Tinea pellionella*) and of the false clothes moth (*Hofmannophila pseudopretella*).

The compositions of the invention are therefore preferably used on the one hand for protecting woolen textiles, for example blankets, wool carpets, woolen underwear, woolen clothing, knits and wool-containing textiles such as blends, one component of which is wool, for example blends of wool and other natural fibres, preferably cotton, or of wool and synthetic fibres, and, on the other hand, also for protecting furs and hides from attack by the above-mentioned pests.

The composition comprises additionally suitable known carriers and / or additives for the treatment of wool for protection against keratin digesting insects. Since the treatment of the wool can be performed during the wool dyeing process, the carriers and additives should be suitable for use under the conditions of fibre manufacturing, especially the dyeing process.

The present invention also relates to a process for protecting keratinous material, in particular woolen textiles, from attack by pests that feed on keratin, e.g. moth and moth larvae, which process comprises treating the material to be protected with one or more compositions of the present invention. To this end, the composition of the invention may additionally contain conventional carriers and formulation assistants, and is normally added to a treatment bath which may additionally contain conventional textile assistants and/or dyes and the material to be protected, which is impregnated within said bath. The bath components may be added to the treatment bath separately.

The materials to be protected, in particular textile materials, can be impregnated, such as with hot or cold aqueous dye, in bleaching, chroming or after-treatment baths containing a specific amount of the composition of the invention. Various textile finishing processes are possible, for example the pad or exhaust process.

The treatment is conveniently carried out in the temperature range from 10° to 100° C., in the dye bath preferably in the range from about 60° to 100° C. and in the after-treatment or wash bath preferably in the range from 10° to 70° C., most preferably from 20° to 60° C.

As further assistants there may be added to the treatment baths dispersants, emulsifiers or surfactants provided that a maximum amount thereof is not already present in the composition of the invention. The bath liquor can additionally contain further conventional assistants and also antimicrobial agents and finishing agents, such as, for example, those based on synthetic resins or starch. If the mothproof finishing is carried out together with the dyeing of the material (e.g. wool), the baths additionally can contain the corresponding dyes and, if appropriate, the necessary assistants, e.g. leveling agents. The aqueous treatment baths may contain, for example, surfactants.

If non-aqueous application is made (e.g. solvent application), an appropriate amount of a composition (active ingredient combination) of the invention may also be added to a suitable solvent and the material to be protected may be impregnated with the solution so obtained. The material to be protected is usually simply impregnated with these solutions.

The proofing of the material to be protected may also be combined with a dry cleaning process. To this end, an appropriate amount of a composition of the invention is dissolved in the cleaning agent and the cleaning process is carried out in the usual manner.

However, an amount of an embodied composition of the invention may also be dissolved in a readily volatile solvent and the resultant solution then sprayed onto the substrate to be protected (spray application). Wool-containing textile fabrics, furs and feathers are particularly suitable for this application. The advantage of the spray application is that pollution of the wastewaters is avoided on account of the recovery of the solvent.

In the processes of the present invention, the compositions of the invention may also be used in combination with other protectants which act against insects that feed on keratin, for example with urea derivatives, benzimidazoles, aromatic sulfonamides and phosphoric and phosphonic acid esters.

The amount of a composition of the present invention which is added to the treatment bath or non-aqueous solvent depends on the substrate and the method of application. However, this amount is ordinarily such that, after application to the material which it is desired to protect, the latter contains about 10 to 2000 ppm, preferably 100 to 1000 ppm, of the composition, with the upper limit being largely determined by economic considerations, whereas the lower limit depends on criteria such as the intended breadth and permanency of the protective action.

Accordingly, one embodiment of the present invention is a process for treating wool comprising the step of treating said wool with a composition comprising an effective amount of an N-(2-A-3-B-4-C-benzoyl)-N'-D-N'-(3,5-dimethylbenzoyl)hydrazine to treat wool for protection from keratin digesting insects, wherein A, B, and C are independently selected from halogens, $(C_1-C_4)$alkyls and $(C_1-C_4)$alkoxys, provided that one or two of A, B or C is hydrogen, and wherein D is a branched $(C_4-C_5)$alkyl. Preferably the process treatment is performed in a dye or wash bath in the temperature range from 10° to 100° C.

Another embodiment is a process for treating wool comprising the step of treating said wool in a cleaning process with a composition comprising an effective amount of an N-(2-A-3-B4-C-benzoyl)-N'-D-N'-(3,5-dimethylbenzoyl)-hydrazine to treat said wool for protection from keratin digesting insects, wherein A, B, and C are independently selected from halogens, $(C_1-C_4)$alkyls and $(C_1-C_4)$alkoxys, provided that one or two of A, B or C is hydrogen, and wherein D is a branched $(C_4-C_5)$alkyl, said treating being performed by dissolving said hydrazine in the cleaning agent.

What is claimed is:

1. A composition comprising an effective amount of N'-(3,5-dimethylbenzoyl)-N-(4-ethylbenzoyl)-N'-(tert-butyl)-hydrazine and a treatment bath agent selected from the group consisting of wool treatment carriers; wool treatment additives; dispersants; cleaning agents; emulsifiers; solvents; surfactants; dyes; leveling agents; antimicrobial agents; and finishing agents, to treat wool for protection from keratin digesting insects.

2. The composition of claim 1 wherein the keratin digesting insect is a *Lepidoptera larva*.

3. A process for treating wool comprising the step of treating said wool with N'(3,5-dimethylbenzoyl)-N-(4-ethylbenzoyl)-N'-(tert-butyl)-hydrazine such that from about 10 to about 2000 ppm is imparted to the wool for protection from keratin digesting insects.

4. The process of claim 3 wherein said treating is performed in a dye or wash bath in the temperature range from 10° to 100° C.

5. The process of claim 3 wherein the keratin digesting insect is a *Lepidoptera larva*.

6. A process for treating wool comprising the step of treating said wool in a cleaning process with a composition comprising N'-(3,5-dimethylbenzoyl)-N-(4-ethylbenzoyl)-N'-(tert-butyl)-hydrazine such that from about 10 to about 2000 ppm is imparted to the wool to protect said wool from keratin digesting insects said treating being performed by dissolving said hydrazine in the cleaning agent.

* * * * *